| United States Patent [19] | [11] Patent Number: 4,931,556 |
|---|---|
| Boyer et al. | [45] Date of Patent: Jun. 5, 1990 |

[54] METHOD OF RESOLVING CIS 3-AMINO-4-(2-(2-FURYL)ETH-1-YL)-METHOXYCARBONYLMETHYL-AZETIDIN-2-ONE AND MALIC ACID SALTS THEREOF

[75] Inventors: Brett D. Boyer; Thomas M. Eckrich, both of Indianapolis, Ind.

[73] Assignee: Eli Lilly and Company, Indianapolis, Ind.

[21] Appl. No.: 258,919

[22] Filed: Oct. 17, 1988

[51] Int. Cl.$^5$ .................... C07B 57/00; C07D 405/06
[52] U.S. Cl. .................................................. 540/364
[58] Field of Search ........................................ 540/364

[56] References Cited

U.S. PATENT DOCUMENTS

| 3,980,698 | 9/1976 | Suzuki | 562/571 |
|---|---|---|---|
| 4,072,759 | 2/1978 | Ikezaki | 514/653 |
| 4,665,171 | 5/1987 | Evans et al. | 540/364 |
| 4,727,146 | 2/1988 | Rice | 546/44 |

OTHER PUBLICATIONS

Medimac, Chem. Abs. 83, 58665a (1975).
Chem. Abs. 89, 43876 (1978), Shiozawa, Chem. Abst. 109, 128823g.
Hatanaka et al., "A Simple Synthesis of (±)-1-Carbacephem Derivatives", *Tetrahedron Letters*, vol. 24, No. 44, pp. 4837–4838 (1983).

*Primary Examiner*—Mark L. Berch
*Attorney, Agent, or Firm*—Bernard J. Graves, Jr.; Leroy Whitaker

[57] ABSTRACT

Cis $\alpha\alpha/\beta\beta$-3-amino-[2-(2-furyl)eth-1-yl]-1-methoxycarbonylmethyl-azetidin-2-one is resolved via optically active malic acid.

2 Claims, No Drawings

METHOD OF RESOLVING CIS 3-AMINO-4-(2-(2-FURYL)ETH-1-YL)-METHOXYCARBONYLMETHYL-AZETIDIN-2-ONE AND MALIC ACID SALTS THEREOF

BACKGROUND OF THE INVENTION

An important clinical trial candidate, (6R, 7S) 7-(R)-phenylglycylinamido-3-chloro-1-azabicyclo[4.2.0]-oct-2-en-8-on-2-carboxylic acid (loracarbef) may be synthesized by various routes. One of the more noteworthy total syntheses of loracarbef is that made possible by Evans and Sjogren, U.S. Pat. No. 4,665,171. The Evans and Sjogren methodology provides a chiral 2+2 (ketene plus imine) cycloaddition, and accordingly, entry to a wide variety of chiral cis β-lactams. However, the Evans and Sjogren methodology provides for the utilization of a chiral auxiliary of the formula

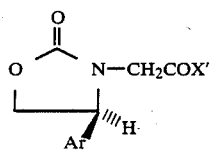

in the 2+2 cycloaddition with a Schiff's base, wherein X' is chloro, bromo, trifluoroacetoxy, or $-OP(=)X_2$, wherein X is halogen. The above chiral auxiliary is synthesized in seven steps from L-phenylglycine. The resulting cycloaddition provides compounds of the formula

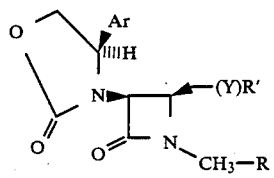

wherein Ar is phenyl, $C_1$-$C_4$ alkylphenyl, halophenyl, $C_1$-$C_4$ alkoxyphenyl, naphthyl, thienyl, furyl, benzothienyl, or benzofuryl; R is phenyl, $C_1$-$C_4$ alkylphenyl, $C_1$-$C_4$ alkoxyphenyl, or halophenyl; Y is $-CH=CH-$, or $-CH_2-CH_2-$; and R' is phenyl, $C_1$-$C_4$ alkylphenyl, $C_1$-$C_4$ alkoxyphenyl, halophenyl, furyl or naphthyl.

The obvious shortcomings of the Evans and Sjogren route are that a very expensive starting material, L-phenylglycine, is used, the chiral auxiliary is synthesized in several steps in linear fashion; and further, the chiral auxiliary is removed and discarded using $Li/NH_3/t$-$C_4H_9OH$ to provide a free 3-aminoazetidinone.

As an achiral alternative, Hatanaka et al., Tetrahedron Letters Vol. 24, No. 49, pp 4837-4838 (1983), provides a method of preparing a 3-hydroxy(±)-1-carbacephalosporin via a 2+2 cycloaddition much in the same fashion as that of Evans and Sjogren, but without the use of a chiral auxiliary as the ketene source. The Hatanaka methodology provides many of the same intermediates as does the Evans and Sjogren synthesis, albeit in achiral form. The advantage of the achiral synthesis is economy of steps and starting material.

The present invention affords a useful alternative to the challenge of synthesizing 1-carba(1-dethia)cephalosporins by providing a method for resolution of a key achiral cis-azetidinone intermediate provided by achiral cis-2+2 cycloaddition. In particular, the present invention provides a method for resolution of a crucial achiral intermediate in the total synthesis of 1-carba(1-dethia)cephalsoporins using L-malic acid.

SUMMARY

Cis 3-amino-4-[2-(2-furyl)eth-1-yl]-1-methoxycarbonylmethyl-azetidin-2-one is resolved by the practice of this invention into its enantiomeric cis α,α and cis β,β components whereby the desired cis β,β enantiomer is selectively crystallized from solution using S(−)-malic acid.

DESCRIPTION OF THE INVENTION

The present invention provides a method of resolving cis α,α/β,β azetidinone represented by the following two enantiomers:

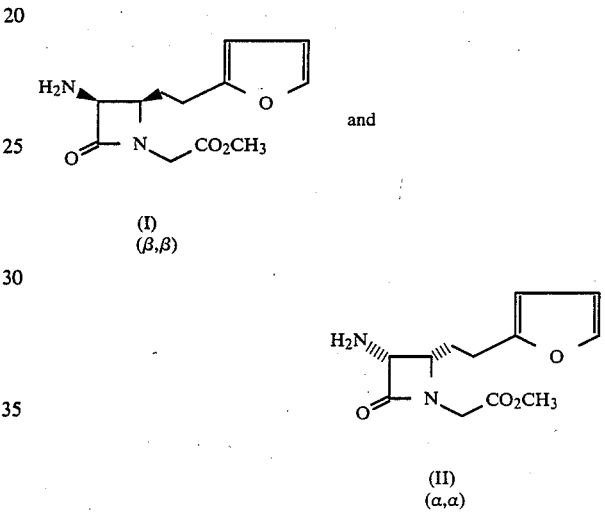

to yield optically pure isomers, each free of the other. This resolution is accomplished by dissolving a racemic mixture of I and II in a polar organic solvent, preferably tetrahydrofuran, and warming the solution to approximately 50° C. or at least a temperature sufficient to dissolve the racemate (I and II) and the malic acid. S(−)-malic acid is then added and the solutions allowed to cool to room temperature gradually overnight, thus forming the diasteromenic S(−)-malic acid salt of (I) in excellent yield and outstanding optical purity. The resulting free amino enantiomer (I) is then provided by standard acid/base workup. Order of addition to the polar organic solution is, of course, not critical.

The corresponding α,α enantiomer (II) is provided by the same manipulations as above by merely substituting R-(+) malic acid for S(−)-malic acid.

Alternatively, in a method to provide optically pure cis β,β isomer, one could use R-(+)-malic acid as the resolving agent and exhaustively crystallize the cis α,α isomer away from the solution, thereby leaving the mother liquors with an enhanced concentration of cis β,β isomer.

As a further aspect of the present invention, in addition to the process for resolving the racemic mixture of I and II above, there is provided the S(−)-malic acid salt of (I) and the R(+)-malic acid salt of (II).

The diastereomeric salt formed is separated from the resolution mixture and the free amino azetidinone is recovered from the salt form by conventional methods. For example, the salt is treated in an aqueous medium with a base to form the free amine which can be extracted from the aqueous phase with a water immiscible solvent such as ethyl acetate. The process provides a high degree of separation of the two enantiomeric azetidinones as reflected by the observed enantiomeric excess (ee) of the product.

It is noteworthy that a number of optically active acids were tried as potential resolving agents albeit none were successful except for malic acid. These acids include: D-(−)-mandelic acid, d-10-camphorsulfonic acid, (+)-tartaric acid, dibenzoyl-(1)-tartaric, ditoluyl-(D)-tartaric, N-benzoyl alanine (L), quinic acid, α-camphoric, L-pyroglutamic, (−)pinane carboxylic acid, and abietic acid. Thus, the two optically pure malic acids ((+) and (−)) appear to be unique as readily available, efficient resolving agents for cis-3-amino-4-[2-(2-furyl)eth-1-yl]-1-methoxycarbonylmethyl-azetidin-2-one.

In each of the resolution attempts, four solvents were evaluated: tetrahydrofuran, ethyl acetate, acetonitrile, and 1,2-dichloroethane. As noted above, only malic acid was shown to be an effective resolving agent, and further, only in tetrahydrofuran. However, one skilled in the art will recognize that the possibility exists that the diastereomer formed by admixture of S(−)-malic acid and (I) (or R(+)-malic and II) may also selectively crystallize from other solvents of like polarity and solvent effects. In this regard, it must be emphasized that the choice of solvent systems in the above is by no means exhaustive and others may be considered to be equivalent in their utility.

One skilled in the art will appreciate that the selective crystallization of one diastereomer from a polar organic solution is also affected by concentration. A relatively low concentration provides pure diastereomer of generally higher purity but lower yield, while the utilization of a higher concentration of racemate and resolving agent will normally provide higher yields of solid, many times at the expense of optical purity. Thus, the preferred concentration range for the present invention in tetrahydrofuran is about 0.25M to about 0.75M, preferably about 0.5M.

The invention is further described by the following examples but is not to be construed as limiting any aspect of the invention.

EXAMPLE 1

A 0.5 g portion of the oxalate salt of cis αα/ββ, 3-amino-4-[2-(furyl)ethyl]-1-methoxycarbonylazetidin-2-one was slurried in 10 ml of water, neutralized to pH=7.5 with saturated $NaHCO_3$ solution and extracted with $CH_2Cl_2$. The $CH_2Cl_2$ solution was dried over anhydrous $MgSO_4$, filtered, and concentrated in vacuo to provide the racemic free-amine.

A 0.232 g sample of the resulting racemic free amine was then dissolved in tetrahydrofuran (2 ml) and heated to about 50° C. A 0.134 g portion of S(−)-malic acid was then added and the resulting solution was allowed to stand overnight.

The containing vessel was wrapped in insulation, thereby allowing the solution to gradually cool to room temperature. The resulting crystalline solid was then filtered and washed with 1 ml tetrahydrofuran to provide 40 mg (22% yield) of the S(−)-malic acid salt of cis β,β-3-amino-4-[2-(2-furyl)eth-1-yl]-1-methoxycarbonylmethyl-azetidin-2-one.

5 mg (14 μm) of the L-malic salt was dissolved in a mixture of 1 ml $H_2O$, 3.5 mg (3 meq) $NaHCO_3$, and 1 ml acetonitrile. 3.2 mg (14 μm) 3,5-dinitrobenzoyl chloride was added and the reaction stirred for 16 hr at room temperature. After 5 ml $H_2O$ was added, the reaction was vacuum filtered and washed with $H_2O$ (2×1 ml portions), cold isopropanol (2×1 ml portions) and diethyl ether (2×2 ml) to isolate 2.5 mg of the 3,5-dinitrobenzamide (85 area % by gradient reverse phase HPLC).

The amide solution in tetrahydrofuran was injected on both a YMC-AKO3S-5300A, 25 cm, 4.6 mm OD chiral column (YMC Corporation) and a Pirkle covalent D-naphthylalanine chiral column (Regis) to show a 99% ee (enantiomeric excess). Also, the ββ-DNB amide made from a chiral β-lactam made by the Evans and Sjogren route and the analogous racemic DNB amide was injected on both systems to confirm the retention times of both the ββ- and the αα-DNB amides.

EXAMPLE 2

The procedure for isolation of the α,α isomer was identical to that of Example 1, substituting R(+)-malic acid as resolving agent to provide the α,α isomer (27% yield, 99% ee).

We claim:

1. The S(−)-malic acid salt of cis ββ-3-amino-4-[2-(2-furyl)eth-1-yl]-1-methoxycarbonylmethyl-azetidin-2-one.

2. The R(+)-malic acid salt of cis αα-3-amino-4-[2-(2-furyl)eth-1-yl]-1-methoxycarbonylmethyl-azetidin-2-one.

* * * * *